United States Patent
Klemm et al.

(10) Patent No.: US 9,089,390 B2
(45) Date of Patent: Jul. 28, 2015

(54) METHOD FOR DETERMINING A PATTERN USE OF AN ELECTRIC TOOTHBRUSH AND ELECTRIC TOOTHBRUSH

(75) Inventors: Torsten Klemm, Eschborn (DE); Matthias Schiebahn, Bad Camberg (DE); Frank Stefan Skopp, Eschborn (DE); Leo Faranda, Rodgau (DE)

(73) Assignee: Braun GmbH, Kronberg (DE)

( * ) Notice: Subject to any disclaimer, the term of this patent is extended or adjusted under 35 U.S.C. 154(b) by 373 days.

(21) Appl. No.: 13/221,961

(22) Filed: Aug. 31, 2011

(65) Prior Publication Data

US 2012/0024323 A1 Feb. 2, 2012

(30) Foreign Application Priority Data

Mar. 18, 2010 (WO) .................. PCT/IB2010/051192

(51) Int. Cl.
*A46B 13/00* (2006.01)
*A61C 17/22* (2006.01)
*A61C 17/34* (2006.01)

(52) U.S. Cl.
CPC ................ *A61C 17/221* (2013.01); *A61C 17/22* (2013.01); *A61C 17/34* (2013.01); *A61C 17/3472* (2013.01); *A61C 17/3436* (2013.01); *A61C 17/3463* (2013.01)

(58) Field of Classification Search
CPC .................................................... A61C 17/221
USPC ........................................................ 15/22.1
See application file for complete search history.

(56) References Cited

U.S. PATENT DOCUMENTS

| | | | | |
|---|---|---|---|---|
| 4,698,869 A * | 10/1987 | Mierau et al. | ................... | 15/22.1 |
| 5,493,747 A | 2/1996 | Inakagata et al. | | |
| 5,784,742 A * | 7/1998 | Giuliani et al. | ................ | 15/22.1 |
| 5,815,872 A * | 10/1998 | Meginniss, III et al. | ........ | 15/22.1 |
| 2005/0268409 A1* | 12/2005 | Blaustein et al. | .............. | 15/22.1 |
| 2006/0010622 A1* | 1/2006 | Naruse et al. | ................... | 15/22.1 |
| 2011/0010876 A1* | 1/2011 | Iwahori et al. | .................. | 15/22.1 |

FOREIGN PATENT DOCUMENTS

| | | |
|---|---|---|
| DE | 44 26 446 A1 | 2/1995 |
| DE | 196 27 752 A1 | 1/1998 |
| DE | 198 40 684 A1 | 3/2000 |

OTHER PUBLICATIONS

International Search Report for PCT/IB2010/051192, Case Z-8360Q dated Jul. 29, 2010.

* cited by examiner

*Primary Examiner* — Hezron E Williams
*Assistant Examiner* — Mark A Shabman
(74) *Attorney, Agent, or Firm* — Alexandra S. Anoff

(57) ABSTRACT

A method for determining a pattern of use of an electric toothbrush is disclosed. The method includes the steps of providing an electric toothbrush including a drive shaft for coupling to a brush part; an electric motor and a drive for providing a first motion of the drive shaft; measuring a characteristic parameter of the electric motor; detecting a distinctive change of the characteristic parameter; and evaluating the distinctive change.

14 Claims, 3 Drawing Sheets

METHOD FOR DETERMINING A PATTERN USE OF AN ELECTRIC TOOTHBRUSH AND ELECTRIC TOOTHBRUSH

CROSS REFERENCE TO RELATED APPLICATIONS

This application is a continuation of International Application No. PCT/IB2010/051192, filed Mar. 18, 2010, the substance of which is incorporated by reference in its entirety herein.

FIELD OF THE INVENTION

The present disclosure relates to a method for determining a pattern of use of an electric toothbrush, wherein the electric toothbrush includes a drive shaft for coupling to a brush part, an electric motor and a drive for providing a first motion of the drive shaft. More particularly, the present disclosure relates to an electric toothbrush including a drive shaft for coupling to a brush part, an electric motor, a drive for providing a first motion of the drive shaft.

BACKGROUND OF THE INVENTION

DE 196 27 752 A1 discloses an electric toothbrush comprising a handle and a brush part. An electric motor is located in the handle. A drive shaft protrudes from the handle and may be coupled to the electric motor. A brush part can be attached to the handle. The brush part further comprises a carrier for the bristles, which may be mechanically coupled to the drive shaft. When in operation the carrier for the bristles performs a rotational motion as well as a translational or swinging motion wherein the frequency of the swinging motion is larger than the frequency of the rotational motion.

In order to avoid damages when the contact pressure between the bristles and the user's teeth exceeds a certain predetermined value DE 196 27 752 A1 further describes that the swinging motion of the carrier for the bristles is interrupted when the contact pressure exceeds a certain predetermined value. As the interruption of the swinging motion according to DE 196 27 752 is achieved mechanically by disengaging an eccentric providing the swinging motion of the drive shaft an acoustical or optical signalling of the contact pressure exceeding a critical value to the user is achieved by mechanically activating an electrical switch.

SUMMARY OF THE INVENTION

In one embodiment, a method for determining a pattern of use of an electric toothbrush is provided. The method includes the steps of providing an electric toothbrush including a drive shaft for coupling to a brush part; an electric motor and a drive for providing a first motion of the drive shaft; measuring a characteristic parameter of the electric motor; detecting a distinctive change of the characteristic parameter; and evaluating the distinctive change.

In another embodiment, an electric toothbrush is provided. The electric toothbrush includes a drive shaft for coupling to a brush part; an electric motor; a drive for providing a first motion of the drive shaft; a measuring device arranged for measuring a characteristic parameter of the electric motor; and a processor arranged for detecting a distinctive change of the characteristic parameter and for evaluating the distinctive change.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
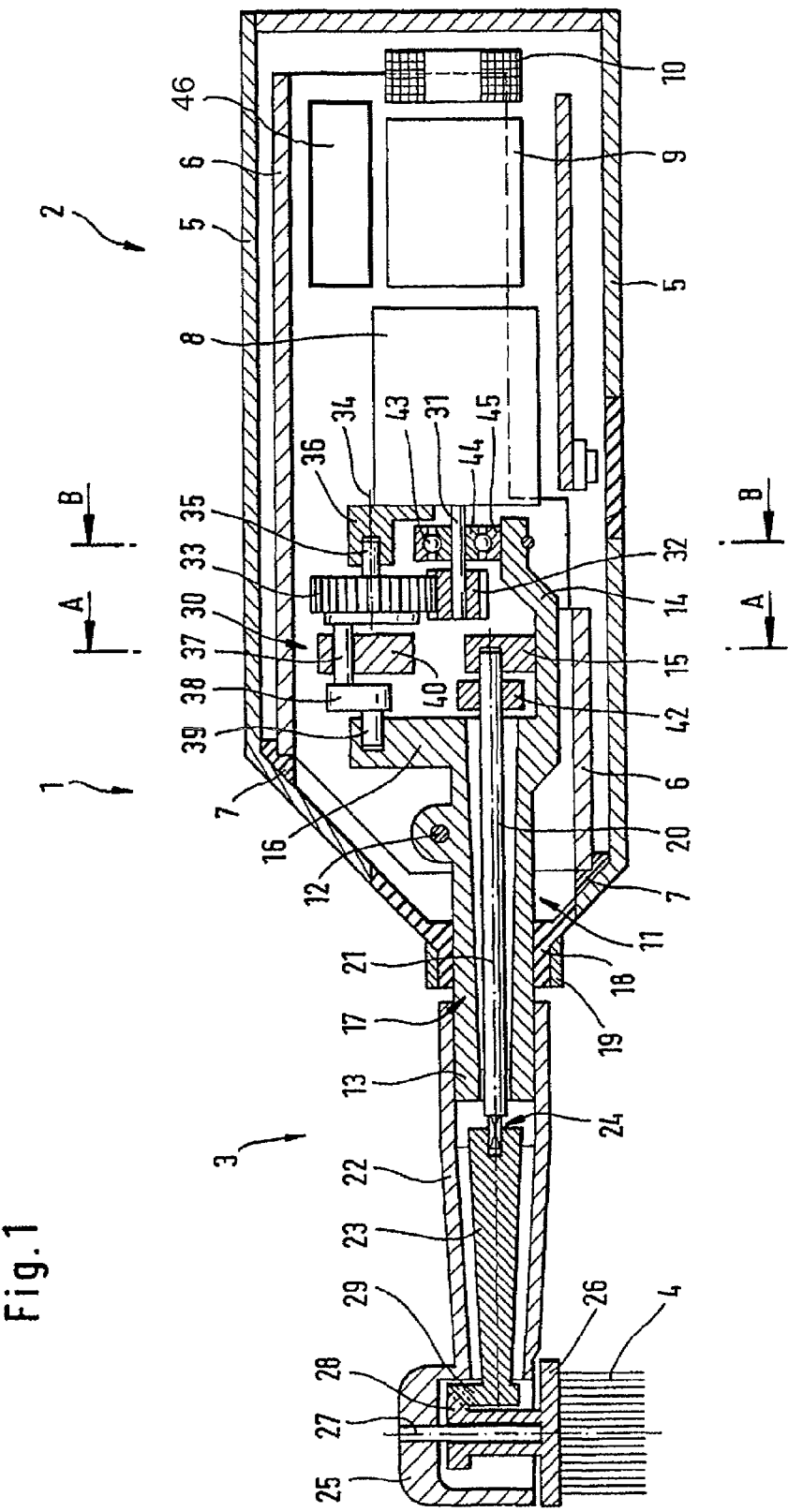
FIG. 1 shows a schematic cross-sectional view of an electric toothbrush according to embodiments shown and described herein.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, a method and a toothbrush allowing a simplified determination of a pattern of use of an electric toothbrush is provided. In another embodiment, a method and a toothbrush allowing a simplified recognition of the contact pressure exceeding a certain predetermined value is provided. In a further embodiment, a method and an electric toothbrush having a reduced number of parts, and in particular saving an electric switch for indicating an excess contact force is provided.

In one embodiment, an electric toothbrush includes a drive shaft for coupling to a brush part, an electric motor and a drive for providing a first motion of the drive shaft. In another embodiment, a method includes the steps: measuring a characteristic parameter of the electric motor, detecting a distinctive change of the characteristic parameter, and evaluating the distinctive change. The characteristic parameter of the electric motor represents the pattern of use of the toothbrush. For example, the contact pressure of the brush exerted on the teeth acts on the rotational speed of the brush. Changes in the characteristic parameter are indicating particular conditions of the brush and therefore allow for determining a pattern of use of the electric toothbrush.

According to one embodiment, the pattern of use is thus determined by detection of distinctive changes of the characteristic parameter due to a particular state of the toothbrush rather than by a comparison of the absolute value of the characteristic parameter with a threshold value. In an embodiment, the drive is arranged to provide a first motion and a second motion of the drive shaft wherein the drive is arranged such that the second motion is interrupted when a predetermined contact pressure is exceeded. In a particular further embodiment, the first motion is a rotational motion and the second motion is a swinging motion.

In an embodiment of an electric toothbrush used for implementing the method, the rotational motion and the swinging motion of the drive shaft are provided by a single electric motor and a drive splitting in the rotational motion of the electric motor into an oscillating rotational motion and a swinging motion of the drive shaft. In another embodiment, the swinging motion can be a translational motion or a pivoting motion of the drive shaft essentially in a direction perpendicular to the axis of rotation of the drive shaft. In a further embodiment, the drive shaft is arranged such that it can be mechanically coupled to a brush part including a carrier for bristles to which multiple bristles are attached.

During operation the electric motor via the drive provides for a rotational, for example, an oscillating rotational motion of the carrier for the bristles attached to the drive shaft and in addition for a swinging motion of the carrier for the bristles parallel to the axis of rotation of the carrier for the bristles such that the bristles carry out a picking motion further to their rotational motion.

In one embodiment, the drive shaft is mounted such that it can be pivoted around a pivoting point. The swinging motion of the drive shaft is then provided by an eccentric being coupled to the electric motor and engaging with the drive shaft or an element attached to the drive shaft. In one embodiment the eccentric or an element connected to the eccentric are spring biased towards the drive shaft or an element connected to the drive shaft.

Whenever a torque is applied to the drive shaft in a direction perpendicular to the axis of rotation and which exceeds the torque provided by the biasing spring the form fit or press fit between the eccentric and the drive shaft or an element coupled to the drive shaft is interrupted and thus the swinging motion of the drive shaft is stopped or interrupted. In this embodiment, the force of the biasing spring predetermines the critical contact pressure between the bristles and the user's teeth. When this critical contact force is exceeded the swinging or translational motion of the drive shaft is interrupted.

In order to allow for a signalling to the user of the toothbrush when the critical contact pressure is exceeded the method according to the present disclosure measures the characteristic parameter of the electric motor, detects a distinctive change in the characteristic parameter and evaluates the distinctive change. In one embodiment, this detection and evaluation of a distinctive change in the characteristic parameter makes an electric switch for signalling to the user redundant.

In one embodiment, the characteristic parameter measured is the voltage induced by the electric motor or its derivative. An induced voltage may either be measured directly or can be derived from the electric motor equation when the other parameters of the equation are known. In an embodiment in which the electric motor is driven by a pulse-width modulation (PWM) signal the voltage induced by the electric motor or its derivative may be measured in-between two driving electric pulses. In another embodiment, the characteristic parameter may be the rotational frequency of the electric motor or its derivative measured by means well known from the prior art, for example, a magneto-restrictive rotational speed sensor.

The method according to one embodiment, can be used for applications in which the electric motor is driven by a constant driving signal such that the rotational frequency of the electric motor depends on the load applied to the motor. Alternatively, it can as well be used for applications in which the rotational frequency of the electric motor is kept constant irrespective of the load applied to the motor, for example, by a PID element (Proportional-Integral-Derivative element).

In an embodiment using a pulse-width modulation signal for driving the electric motor while keeping the rotational frequency of the electric motor constant, the characteristic parameter of the motor measured can be the duty factor of the pulse-width modulation signal or its derivative. The duty factor of a pulse-width modulation signal according to the present disclosure is the time for which signal is on, divided by the period of the signal. When the rotational frequency is kept constant the duty factor provides a clear indication for the load applied to the motor.

In a further embodiment, the characteristic parameter determined may be the commutation frequency of the electric motor or its derivative being characteristic for its rotational frequency. In one embodiment it is assumed that the characteristic parameter of the electric motor well represents its load and therefore is a measure for the contact pressure applied to the brush and in turn via the drive to the motor. For example, the interruption of the translational motion of the drive shaft when the predetermined contact pressure is exceeded leads to a distinctive change in the characteristic parameter clearly identifying the interruption of the translational motion and thus the crossing of the predetermined critical contact pressure.

In one embodiment, the detection of a distinctive change of the characteristic parameter comprises the steps: recording the characteristic parameter over time, and comparing the recorded characteristic parameter with a predetermined progress of the characteristic parameter. Such comparison may, for example, be carried out by comparison of the measured and recorded characteristic parameter to values stored in a look-up table or a comparison of a stored progression of the characteristic parameter in form of an equation describing its development over time or contact pressure. Recording of the characteristic parameter may, for example, be carried out by storing the measured value versus time in a storage.

Alternatively or additionally, the method according to one embodiment may include the steps of determining the slope of the characteristic parameter and detecting a subsequent occurrence of slopes having opposite signs. In a further embodiment, the derivative, i.e. the slope, of one of the above mentioned parameters may be measured directly as the characteristic parameter of the electric motor. The changes in the characteristic parameter may then for example be detected as described above by recording the parameter versus time.

Alternatively, one may omit recordation of the parameter and detect the occurrence of a change in sign of the derivative whenever occurring between two measurements. For example, in one embodiment, the rotational frequency of the electric motor decreases when the contact pressure is increased by a user of the toothbrush by pressing the bristles to the teeth harder and harder. The rotational frequency decreases over time until the swinging motion provided by the electric motor via the drive is interrupted leading to a reduced overall load on the electric motor and thus to an increase of the rotational frequency of the electric motor. As a result, right after the interruption of the translational motion an increase of the rotational frequency over time can be observed. As the two slopes of the rotational frequency before and after interruption of the swinging motion are characteristic for the decoupling of the swinging motion the determined slopes identify the excess of the critical contact pressure and allow for a respective signalling to the user.

According to a further embodiment, the distinctive changes of the characteristic parameter are evaluated to determine a figure of merit for the usage of the toothbrush. In an embodiment, this figure of merit may be determined by evaluating or counting the number of times at which a distinctive change, for example, an excess of the critical contact pressure, occurs. This number then forms the figure of merit. The lower it is the better the brush has been used. In a further embodiment, the figure of merit is signalled to the user. In one embodiment, the number of times at which the critical contact pressure had been exceeded to the user at the end of each cycle of use may be displayed, for example, when finishing brushing of the teeth.

In an alternative embodiment, signalling of the figure of merit to the user is achieved by representation in the form of light emitting diodes (LEDs), wherein for example, each diode represents a certain threshold value. In an example, a green LED denotes that the critical contact pressure was never exceeded, an orange LED denotes that the critical contact pressure was exceeded three times or less and a red LED denotes that the critical contact pressure was exceeded more than three times.

In one embodiment, an electric toothbrush including a drive shaft for coupling to a brush, an electric motor, a drive for providing a first motion of the drive shaft, a measuring device arranged for measuring a characteristic parameter of the electric motor, and a processor arranged for detecting a distinctive change of the characteristic parameter and for evaluating the distinctive change is provided. In one embodiment the measuring device, the recorder and the processor are embodied in a microcontroller.

Insofar as the above embodiments can at least partially be realized by a software controlled processor it is apparent that a computer program which provides such control and a storage medium on which such a computer program is stored are considered aspects of the present disclosure.

The electric toothbrush 1 depicted in FIG. 1 is provided for cleaning the teeth of a user, in particular for removing plaque from the surfaces of the teeth. The electric toothbrush includes a handle 2 having an elongated approximately cylindrical form. A brush part 3 may be attached to the handle 2. The diameter of the handle 2 is chosen such that the user of the electric toothbrush 1 can hold it safely at the handle 2. In one embodiment, the diameter of the brush part 3 is smaller than the diameter of the handle 2 for an enabling insertion of the brush part 3 in the mouth of the user. At the free end of the brush part 3 numerous bristles 4 may extend which may be used to clean the teeth of the user.

In one embodiment, handle 2 includes a housing 5 in which a chassis 6 is located. The chassis 6 has an elongated essentially cylindrical form and extends over almost the entire length of the housing 5 and therefore the handle 2. The chassis 6 carries an electric motor 8, an accumulator 9, as well as further electronic elements such as a charging coil 10 and a controller 46. The chassis 6 furthermore includes an oscillating crank 11 being pivotable around a pivot axis 12. The crank 11 as well as the pivot axis 12 is located in the part of the handle 2 facing to the brush part 3. The crank 11 partially extends over the handle 2.

Further parts of the crank 11 may include a tube 13, a cantilever 14 and two carrying elements 15, 16. The tube 13 of the crank 11 extends through an opening 17 of the handle 2 wherein between the tube 13 and the housing 5 of the handle 2 an annular membrane 18 made of rubber is located in order to provide an elastic feed through of the tube 13 through the opening in the handle 2. The brush part 3 can be attached to the part of the tube 13 extending over the housing 5. The brush part 3 attached to the crank 11 extends the crank 11 towards the bristles 4.

In the tube 13 of the crank 11 a drive shaft 20 may be located which at its end facing away from the handle can be attached to a further shaft 23 mechanically connected to the bristles 4. In one embodiment, the drive shaft 20 is mounted rotatably around an axis of rotation 21 in the tube 13 as well as on the carrying element 15.

The pivot axis 12 of the crank 11 and the axis 21 of the drive shaft 20 are arranged approximately orthogonal to each other around the axis of rotation 21. In one embodiment, the brush part 3 includes a carrying tube 22 in which the brush shaft 23 is pivotably mounted. When the brush part 3 is clipped on the housing 2 the brush shaft 23 is concentric to the drive shaft 21 and the drive shaft 21 engages the brush shaft 23 in a recess 24 providing a form fit transmission. In one embodiment, a shell 25 is located at the free end of the brush part 3. A bristle carrier 26 including numerous bristles 4 is located in the shell 25. The bristle carrier 26 is pivotably mounted on an axis 27. The axis 27 is approximately parallel to the bristles 4 and perpendicular to the brush axis 23 as well as to the drive shaft 21. There are two bevel gear segments such that an alternating rotational motion of the brush shaft 23 around the axis 21 can be transformed in an alternating rotational motion of the bristle carrier 26 around the axis 27.

In one embodiment, a four bar chain 30 is located between the crank 11 and the electric motor 8 in the handle 2. In order to form the four bar chain 30, the electric motor 8 includes a motor shaft 31 which is approximately parallel to the axis 21 of the drive shaft 20 and extends over the electric motor 8. The gear wheel 32 mounted to the motor shaft 31 is cogging a spur gear 33. The spur gear 33 is rotatably mounted on a pin 35 on an axis 34. The pin 35 is mounted in a carrying element 36 attached to the electric motor 8. The spur wheel 33 may further include an eccentric crank being mounted to the spur wheel 33 in a distance from the axis 34. In one example, the shaft 37 is further rotatably mounted via connecting element 38 and a pin 39 in the carrying element 16 of the crank 11. In one example, the pin 39 is concentric to the axis 34 formed by the pin 35.

Figure 2:
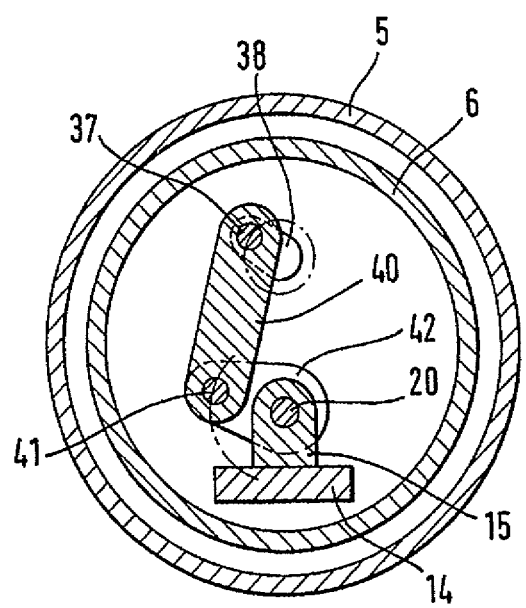
FIG. 2 shows a cross-sectional view of the toothbrush in FIG. 1 along a line A-A.

In one embodiment, on the shaft 37 a connection rod 40 is rotatably mounted. As depicted in FIG. 2 the connecting rod 40 is pivotably mounted by a pin 41 to a driving shaft 42. The driving shaft 42 is torque-proof mounted to the shaft 20 of the crank 11 between the tube 13 and the carrying element 15. On the motor shaft 31 of the electric motor 8, a ball bearing 43 is located. The ball bearing 43 comprises an eccentric inner ring 44 and a concentric outer ring 45. With the eccentric inner ring 44 the ball bearing 43 is fitted on the motor shaft 31. The eccentric inner ring 44 thus operates as an eccentric. In one embodiment, the concentric outer ring 45 abuts on the cantilever 14 of the crank 11.

In one embodiment, the cantilever 14 of the crank 11 is spring biased against the outer ring 45 of the ball bearing 43. Thus when operating the electric motor 8 provides a rotational motion of the motor shaft 31 in a single direction which is then transformed into an alternating rotational motion of the drive shaft 20 and a simultaneously into a swinging motion of the drive shaft 20 around the pivot axis 12. The electric toothbrush is controlled by an electronic controller 46 including the necessary elements for providing an electric drive signal to the motor 8. The controller 46 furthermore provides the elements which are necessary to implement the method according to one embodiment. Furthermore the controller 46 controls the signalling of the user.

In operation, when the torque caused by the force acting on the carrier 26 for the bristles 4 exceeds the torque caused by the biasing force pressing the cantilever 14 towards the outer ring 45 of the ball bearing 43 the engagement between the eccentric formed by the ball bearing 43 and the cantilever 14 is interrupted such that the swinging motion of the drive shaft 20 around the pivot axis 12 in turn is also interrupted. This interruption of the swinging motion of the drive shaft 20 is now used for a signalling to the user of the toothbrush 1 that a critical contact force of the bristles with the user's teeth is crossed by measuring and analysing a characteristic parameter of the electric motor over time, wherein the analysis includes the steps of detecting distinctive changes of the characteristic parameter and evaluating those changes.

Figure 3:
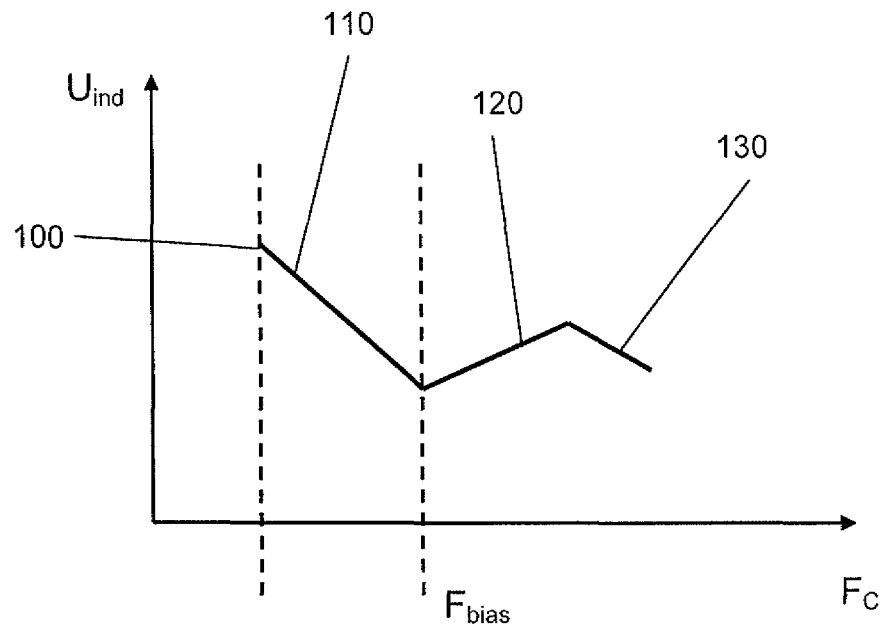
FIG. 3 shows a schematic diagram of the rotational frequency over the contact pressure.

In a first embodiment the electric motor 8 is powered by a constant pulse-width modulation signal and the back EMF, i.e. the voltage induced by the electric motor 8 is measured as the characteristic parameter during subsequent points in time for which the pulse-width modulated signal is low. The induced voltage as a characteristic parameter of the electric motor is a good measure for the rotational frequency of the electric motor 8. In FIG. 3, the induced voltage $U_{ind}$ is plotted over the contact pressure $F_c$ applied to the bristle carrier 26. Assuming that the contact pressure is increased linearly over time, the axis could also denote time. Disregarding any effects when switching on the electric toothbrush it is assumed that the bristles are initially brought into engagement with the teeth of the user with a moderate force leading to a level of the induced voltage $U_{ind}$ 100. Assuming that the contact pressure $F_c$ is then increased, the induced voltage $U_{ind}$ in section 110 of the graph plotted in FIG. 3 decreases providing the graph with a negative slope. When the torque induced by the contact pressure $F_c$ exceeds the torque induced by the biasing force of the spring pushing the cantilever 14 towards the outer ring 45 of the ball bearing 43 the engagement between the eccentric and the cantilever 14 is interrupted. When this occurs the swinging motion of the drive shaft stops leading to a situation in which the torque of the electric motor is entirely transferred to the rotational motion of the brush. This in turn leads to an increasing rotational frequency and to an increase of the induced voltage $U_{ind}$ denoted by 120 in FIG. 3. If the contact pressure between the bristles and the user's teeth is further increased at a certain stage, the rotational frequency and thus the voltage induced by the electric motor 8 drops again if the contact pressure is further increased. This further drop in the voltage induced is denoted by 130 in FIG. 3.

According to one embodiment, the induced voltage $U_{ind}$ is recorded over time and from the recorded curve which corresponds to the plot in FIG. 3, a characteristic behaviour, i.e. a distinctive change in the slope, is detected which unambiguously identifies the interruption of the swinging motion of the drive shaft 20. In the example shown the identifying portions of the plot are the subsequent sections 110 and 120 having a negative slope followed by positive slope. In another embodiment, the change of a curvature of the graph recorded for the characteristic parameter, i.e. $U_{ind}$, can be taken to identify the interruption of the swinging motion of the drive shaft. In order to be able to clearly identify the bits of the graph which are characterising for the interruption of the swinging motion, and thus for an increase of the contact pressure over a predetermined critical pressure the electronic controller 46 of the toothbrush depicted in FIG. 1 includes a memory 47 in which the characterising bit of the graph identifying the interruption of the swinging motion is stored and during operation of the toothbrush the recorded characteristic parameter over time is compared to the stored values.

Figure 4:
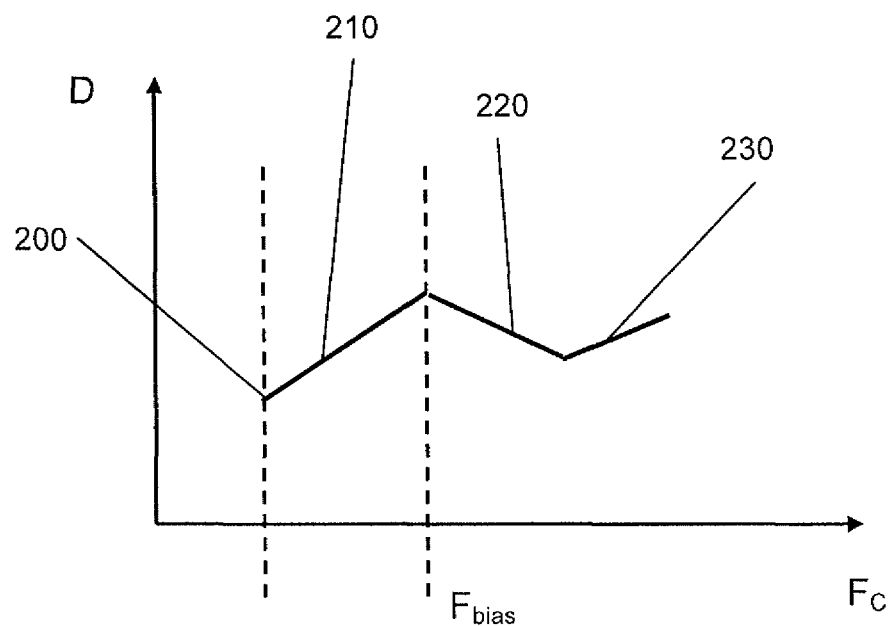
FIG. 4 shows a schematic diagram of the duty factor of a pulse-width modulated driving signal for the electric motor over the contact pressure.

In another embodiment, the rotational frequency of the electric motor of the toothbrush 1 is kept constant and the duty factor of the pulse-width modulation signal supplied to drive the electric motor 8 is measured and recorded over time as the characteristic parameter of the electric motor. The duty factor determined is defined as the ratio between the time over which the signal is high divided by the period of the oscillatory signal. In this embodiment the electric toothbrush comprises a PID element for controlling the rotational frequency of the electric motor. When the contact pressure between the bristles 4 and the user's teeth is increased this leads to a decrease in the rotational frequency of the electric motor. In order to compensate for this decrease the duty factor of the pulse-width modulation signal is increased. This is clearly depicted in FIG. 4 in which duty factor D is plotted over the contact pressure $F_c$ applied to the bristles. As before assuming that the contact pressure is linearly increased over time the X-axis could also be denoted as time.

After initially bringing the bristles in engagement with the teeth at point 200 the duty factor D is increased in section within increasing contract pressure. When the critical contact pressure defined by the mechanical biasing of the cantilever 14 toward the eccentric 43 is reach the rotational frequency would start to increase but is compensated by a decrease on the duty factor of the pulse-width modulation signal as depicted by section 220 of plot in FIG. 4. If the contact pressure is further increased at a certain point in time this leads to the rotational frequency starting to drop again which is then compensated by a further increase of the duty factor of the pulse-width modulation signal denoted by 230 in FIG. 4. As described before for the induced voltage $U_{ind}$ as the characteristic parameter the interruption of the swinging motion of the drive shaft 20 is again identified by a characteristic development of the recorded duty factor around the point in time at which the swinging motion is interrupted.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for determining a pattern of use of an electric toothbrush comprising the steps of:

providing an electric toothbrush including a drive shaft for coupling to a brush part, an electric motor and a drive for providing a first motion of the drive shaft;

measuring a characteristic parameter of the electric motor;

detecting and evaluating a distinctive change of the characteristic parameter comprising the steps of:

recording the characteristic parameter over time;

determining the slope of the characteristic parameter by comparing the recorded characteristic parameter with a predetermined progress characteristic parameter; and detecting a subsequent occurrence of a slope having an opposite sign wherein the distinctive change of the characteristic parameter is detected without comparing an absolute value of the characteristic parameter with a threshold value.

2. A method according to claim 1, wherein the drive is arranged to further provide a second motion of the drive shaft, such that the second motion is interrupted when a predetermined contact pressure of the tooth brush is exceeded.

3. A method according to claim 2, wherein the first motion is a rotational motion and the second motion is a swinging motion.

4. A method according to claim 1, wherein the characteristic parameter is the voltage induced by the electric motor or its derivative.

5. A method according to claim 1, wherein the characteristic parameter is the rotational frequency of the electric motor or its derivative.

6. A method according to claim 1, wherein the characteristic parameter is the duty factor of a pulse-width modulation signal supplied to drive the electric motor or its derivative.

7. A method according to claim 1, wherein the characteristic parameter is the commutation frequency of the electric motor or its derivative.

8. A method according to claim 1, wherein the step of evaluating the distinctive change includes a signalling to the user when a distinctive change of the characteristic parameter is detected.

9. A method according to claim 1, wherein the step of evaluating the distinctive change includes a derivation of a figure of merit for the usage of the toothbrush.

10. A computer program for execution of a method according to claim 1.

11. A computer readable data storage containing a computer program according to claim 10.

12. A microcontroller on which a computer program according to claim 10 is loaded.

13. An electric toothbrush comprising:

a drive shaft for coupling to a brush part;

an electric motor;

a drive for providing a first motion of the drive shaft;

a measuring device arranged for measuring a characteristic parameter of the electric motor; and a processor arranged for detecting a distinctive change of the characteristic parameter and for evaluating the distinctive change according to the method of claim 1.

14. A method for determining a pattern of use of an electric toothbrush comprising the steps of:

providing an electric toothbrush including a drive shaft for coupling to a brush part including a carrier for bristles to which multiple bristles are attached, and an electric motor for providing torque resulting in oscillating rotational motion and swinging motion of the drive shaft;

detecting and evaluating a distinctive change of the characteristic parameter comprising the steps of:

measuring the characteristic parameter with a measuring device;

determining the slope of the characteristic parameter by comparing the recorded characteristic parameter with a predetermined progress characteristic parameter wherein the characteristic is a voltage induced by the electric motor or its derivative; and detecting a subsequent occurrence of a slope having an opposite sign;

evaluating the distinctive change with a processor; and signalling to a user that the distinctive change of the characteristic parameter is detected by interrupting the swinging motion of the drive shaft and entirely transferring the torque of the electric motor to the rotational motion thereby increasing the voltage induced by the electric motor or its derivative;

wherein the distinctive change of the characteristic parameter is detected without comparing an absolute value of the characteristic parameter with a threshold value.

* * * * *